United States Patent [19]

MacKeen

[11] Patent Number: 5,366,739
[45] Date of Patent: Nov. 22, 1994

[54] METHOD OF OPHTHALMIC DRUG DELIVERY

[75] Inventor: Donald L. MacKeen, Bethesda, Md.

[73] Assignee: DEO Corporation, Bethesda, Md.

[21] Appl. No.: 986,932

[22] Filed: Dec. 19, 1992

Related U.S. Application Data

[63] Continuation-in-part of Ser. No. 926,244, Aug. 6, 1992, Pat. No. 5,290,572.

[51] Int. Cl.$^5$ .................. A61K 33/42; A61K 33/06; A61K 33/10
[52] U.S. Cl. .................. 424/602; 424/682; 424/686; 424/687; 424/696
[58] Field of Search ............. 424/602, 686, 687, 682, 424/696; 514/169, 912, 725

[56] References Cited

PUBLICATIONS

Physician's Desk Reference for Ophthamology, 16 Edition, 1988, pp. 13, 153 and 154.
Physician's Desk Reference for Ophthamology, 16 Edition, 1988. pp. 9, 11 and 12.
PTS Newsletter Database. Bausch & Lomb Dry eye Therapy lubricating Eye drops.

*Primary Examiner*—Zohreh Fay
*Attorney, Agent, or Firm*—Raymond B. Cranfill

[57] ABSTRACT

A method for prolonged delivery of a therapeutic agent to the eye is disclosed. The method provides for the addition of a desired drug to a suitable, preferably non-aqueous, vehicle. An amount of the vehicle containing a therapeutic dose of the drug is placed on the extraocular skin adjacent to the lateral canthus of the eye. Movements of the orbicularis oculi associated with the scissor-like closing of the lids of the eye continuously transport small portions of the drug containing vehicle into the interpalpebral space where the drug is released to the cornea for intraocular penetration and treatment effected. The method of the invention is particularly effective in delivering insoluble calcium salts for the treatment of dry eye.

5 Claims, 2 Drawing Sheets

METHOD OF OPHTHALMIC DRUG DELIVERY

The present application is a continuation-in-part of U.S. patent application Ser. No. 07/926,244, filed Aug. 6, 1992, U.S. Pat. No. 5,290,572 issued Mar. 1, 1994.

FIELD OF THE INVENTION

This invention relates generally to the treatment of diseases of the human eye and more particularly to methods of delivering drugs and other agents to the eye for treating various eye diseases.

REFERENCES

Dohlman. 1971. Trans. Ophthal. Soc. U.K. 91:105.
Huth et al. 1981. Arch. Ophthal. 99:1628.
Lamberts. 1980. International Ophthalmology Clinics 20 (3):63.
Lemp. 1972. International Ophthalmology Clinics. 12:221.
Lemp. 1973. International Ophthalmology Clinics. 13:145.
MacKeen. 1980. International Ophthalmology Clinics 20 (3) :79.
Pavan-Langston. 1973. International Ophthalmology Clinics. 13:231.

BACKGROUND OF THE INVENTION

Treatment of diseases of the human eye is often accomplished through the topical administration of therapeutic agents. Any topical method of drug delivery must take into account and attempt to overcome many inherent physiological systems that operate to protect and maintain the vital front surfaces of the eye. For example, the cornea and conjunctiva are coated with mucin and bathed in a complex aqueous fluid derived mainly from the lacrimal glands. The region between the lids of the normal eye—the interpalpebral space—is covered by the preocular tear film, a very thin (generally less than 40μM) liquid layer covering the cornea and conjunctiva. The preocular tear film is provided on its anterior surface with a thin film of lipids derived from the Meibomian glands that open along the lid margin. Because the tear film is dynamic and subject to contamination, the tear film is continually replaced, the effete tear residues being forced from the eye through the pair of puncta and associated canaliculi at the medial corner of the eye by blinking.

In order to have therapeutic effect, a drug or other compound must generally pass into the eye through the cornea. Problematic to topical delivery of drugs is the fact that the cornea is less permeable than the conjunctiva. Further, the surface area of the conjunctiva is highly vascularized, and in surface area is some 14 times greater than the surface area of the cornea. For these reasons, the transconjunctival loss of instilled drugs is considerable. Further, water soluble drugs are quickly eliminated from the eye surface through tear outflow, a process that is often accelerated in the diseased eye, and topical delivery of drugs to the eye in sufficient quantity and for sufficient periods is often difficult. Thus, the effectiveness of prior art methods of topical drug application is often limited.

The most common known topical delivery of ophthalmic drugs is accomplished using water-based compositions, either as a solution or a suspension. Such compositions are generally delivered as drops or as a wash directly to the eye surface. Because such aqueous compositions are quickly eliminated from the eye, various attempts have been made to enhance the contact time and/or drug delivery characteristics by employing a variety of water-soluble polymers, both synthetic and natural. For stability, these water-polymer preparations must contain a preservation system when intended for a. multiple dose use. Further, most compositions must be buffered, usually to an acidic range. Examples of stabilized solutions and tear substitutes are disclosed in U.S. Pat. Nos. 4,407,791 to Stark; 4,409,205 to Shively; and 5,075,104 to Gressel et al. When instilled in the eye, the drug preparation usually overwhelms the resident tear volume, resulting in an initial loss both of some drug and the resident tear constituents. Further, the relatively cool temperature and acidic pH of the drug preparation produces a strong blink reflex coupled with reflex tearing , thereby resulting in further loss of the drug preparation from the eye surface by outflow.

Although the use of aqueous vehicles is a common and widespread means of topical delivery, the use of such a delivery system has resulted in a number of problems. First, the very nature of the delivery system, in particular its aqueous and irritating characteristics, results in a rapid loss of drug from the eye,. necessitating frequent and repetitive reintroduction of the drug-bearing composition to the eye. This is not only inconvenient to the patient, but results in less efficacious treatment because of the difficulty in maintaining a more or less continuous delivery of drug through the cornea to the eye. This difficulty of delivery is further compounded by the loss of drug preparation across the larger and more permeable vascular conjunctival surface. Preservatives and stabilizing compounds can also result in tissue damage to the cornea and conjunctiva.

In attempts to avoid the problems associated with aqueous drug delivery, suspensions of insoluble drug preparations have been used, resulting in longer drug action through the slow dissolution of particles trapped in the cul de sacs. However, the use of ophthalmic suspensions has its own set of problems, primarily inaccurate dosages due to inadequate patient resuspension.

Water-insoluble ointments have also been used as vehicles for drug delivery. However, the use of ointments has many attendant problems, not the least of which is discomfort and loss of visual acuity due to the excessively thick and uneven layer produced by the ointment on the cornea. In addition, ointments are difficult to apply since the delivery method requires application of the ointment to the tarsal conjunctiva of the everted lower lid.

In addition to purely fluid vehicles, such as aqueous solutions, suspensions and ointments, solid vehicles in the form of drug-releasing inserts have also been utilized to deliver drugs to the eye surface. Many of these devices and methods are discussed in Pavan-Langston (1973) and Lamberts (1973). Examples of such inserts include the PVA inserts of Maichuk and the Ocuserts½ of Alza. Some inserts are hydrophilic contact lenses that have been impregnated with a drug that is released to the corneal surface over time after lens insertion. In other cases, the insert actually dissolves slowly to release the drug. The use of inserts however is problematic. They are cumbersome, increase the risk of eye infection by agents carried into the eye on the insert, and are expensive. Further, it is not clear that inserts actually achieve as high or as prolonged a delivery of drug as is sometimes claimed. For example, much of the drug released from an insert is still likely to be taken up by the conjunctiva and pass thereafter into the general circulation with little or no therapeutic benefit for the eye. Further, the irritation resulting from the use of the insert probably results in increased flow of lacrimal fluid, thereby increasing the likelihood that the drug will be washed out of the eye.

A significant problem associated with all known methods of topical drug delivery stems from the muscular coordination required of the patient for self-application. Both soluble aqueous vehicles and aqueous suspensions are generally delivered through drops to the eye. Ointments require precise delivery to the inside portion on an eyelid, while ocular inserts of various types require finger delivery of an object into the eye. Each of these manipulations can be especially difficult for the elderly and can result in serious injury to the eye when the drug is delivered to the eye with too much force.

One ophthalmological disease that has proved especially susceptible to treatment by the method just described is dry eye, (also known as keratoconjunctivitis sicca), is a common ophthalmological disorder affecting millions of Americans each year. The condition is particularly widespread among post-menopausal women due to hormonal changes following the cessation of fertility. It is one of the most common of human eye diseases and is generally treated through the topical delivery of a variety of therapeutic agents.

Dry eye may afflict an individual in varying severity. In mild cases, a patient may experience burning, a feeling of dryness, and persistent irritation when debris lodge between the eye lid and the eye surface. In severe cases, vision may be substantially impaired. Good reviews of dry eye syndrome and standard methods of treatment may be found in Dohlman (1971) and Lemp (1973).

Although it appears that dry eye may result from a number of unrelated pathogenic causes, all presentations of the syndrome share a common effect, the breakdown of the pre-ocular tear film, which results in dehydration of the exposed outer surface and many of symptoms outlined above.

Practitioners have taken several approaches to the treatment of dry eye. One common approach has been to supplement and stabilize the preocular tear film using so-called artificial tears. Another approach has been the use of ocular inserts that function variously to provide a tear substitute or to stimulate endogenous tears.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids. Examples of these treatment approaches are disclosed in U.S. Pat. Nos. 4,131,651 to Shah et al.; 4,370,325 to Packman; 4,409,205 to Shively; 4,744,980 and 4,883,658, both to Holly; 4,914,088 to Glonek; and 5,057,104 to Gressel et al.

United States Patents directed to the use of ocular inserts in the treatment of dry eye include U.S. Pat. No. 3,991,759 to Urquhart. The use of ocular inserts is also discussed in detail in Lamberts (1980).

Another recent approach involves the provision of lubricating substances in lieu of artificial tears. U.S. Pat. No. 4,818,537 to Guo discloses the use of a lubricating, liposome-based composition. U.S. Pat. No. 4,966,773 discloses the use of microfine particles of one or more retinoids.

Aside from the above efforts, which are directed primarily to the alleviation of symptoms associated with dry eye, also known are methods and compositions directed to treatment of the dry eye condition. For example, U.S. Pat. No. 5,041,434 discloses the use of sex steroids, such as conjugated estrogens, to treat dry eye condition in post-menopausal women.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is cumbersome and time consuming, increases the exposure of the eye to preservative agents and can be very expensive.

The use of ocular inserts is also problematic. Aside from cost, they are often unwieldy and uncomfortable. Further, as foreign bodies, they pose a risk of acting as a vector for infectious organisms. In situations where the insert does not itself produce and deliver a tear film, artificial tears must still be delivered on a regular and frequent basis. Indeed, Pavan-Langston (1973) has concluded that, as a rule, ocular inserts are not very effective in the treatment of many dry eye conditions.

In view of the foregoing, there is a clear need for a reliable, effective, method of topical delivery of a therapeutic agent to the cornea that is both easy to administer and long acting.

SUMMARY OF THE INVENTION

It is an object of the invention to provide a easy to administer method of topical delivery of a drug or therapeutic agent to the human eye.

It is yet another object of the invention to provide a method of ophthalmic drug delivery that is capable of delivering doses of a drug to the cornea of the human eye over a prolonged period.

It is another object of the invention to provide a method of extraocular ophthalmic drug delivery.

Still another object of the invention is to provide a method of topical ophthalmic drug delivery that significantly lessens the risk of injury to the eye.

Still another object of the invention is to provide a method of ophthalmic drug delivery this is highly cost effective.

A further object of the invention is to provide a topical method for delivering a drug or other composition for the treatment of dry eye syndrome.

It is yet another object of the invention to provide a composition for the treatment of dry eye that is easy and convenient to administer.

Yet another object of the invention is to provide a composition for the treatment of dry eye that does not require continual or even frequent delivery to the eye in order to be effective.

A further object of the invention is to provide a composition for the treatment of dry eye that is inexpensive.

Still another object of the present invention is to provide a method for utilizing the composition of the invention in the treatment of dry eye syndrome.

The invention meets these objects by an easy to administer, long-acting composition capable of delivering a desired amount of a drug or other therapeutic agent to the cornea of the eye. According to the method of the invention, a desired drug or other compound is mixed with a pharmacologically acceptable carrier to form a desired ophthalmological composition. The carrier is preferably hydrophobic in nature. The composition is then delivered manually or by sterile cotton application to extraocular skin adjacent to the lateral canthus of the eye. Movements of the orbicularis oculi associated with the scissor-like closing of the lids of the eye continuously transport small portions of the composition into the eye where the drug is released to the cornea and treatment effected.

According to another aspect of the invention, the objects regarding the treatment of dry eye syndrome are met by providing a minimally water-soluble, calcium-based composition that is delivered in an appropriate vehicle to the eye according to the delivery method of the invention just described. Calcium in this composition is present as a more or less water insoluble salt, such as calcium carbonate. The calcium salt is very finely divided into particles, preferably in micronized form. The finely divided calcium salt is then dispersed in a pharmacologically acceptable carrier, preferably hydrophobic in character.

It has been discovered that a preferably hydrophobic drug containing vehicle delivered to extraocular skin adjacent to the lateral canthus of the eye will be taken up by and communicated across the surface of the human eye as a result of the scissoring motions of the eye lid during blinking. This method effects the slow and more or less continuous delivery of a desired drug to the eye surface, and ultimately through the cornea and into the eye. The nature of the ophthalmological composition combined with the continuous delivery ensures that a fairly constant amount of the desired therapeutic agent is present in the tear film and in contact with the cornea for a prolonged period. This method is clearly advantageous over the prior art in that continuous delivery of therapeutically efficacious amounts of a desired drug can be delivered over prolonged periods. The method avoids the comfort and visual acuity problems associated with ointments and inserts and greatly lessens the likelihood of injury to the eye in that the ophthalmological composition is not delivered directly to the eye surface. This minimizes system loss of drug across the conjunctiva, maximizing corneal exposure and subsequent drug penetration. Because the composition is preservative-free, the ophthalmic composition of the invention avoids the side effects associated with prior art compositions.

According to another aspect of the invention, it has further been discovered that calcium plays a key role in the development and maintenance of the preocular tear film and that the delivery of a slowly solubilized, salt of calcium according to the general method of the invention not only alleviates symptoms of discomfort and dryness, and conjunctival/lid margin redness, but may help correct underlying physical and physiological deficiencies responsible for certain dry eye condition. The delivery of an insoluble calcium salt according to the method of the invention has shown good effect in alleviating the symptoms of dry for periods of time considerably longer than using conventional delivery systems and with less discomfort to the patient.

These and other objects and advantages of the invention will become more fully apparent after reading the following detailed description of the invention and examples.

DETAILED DESCRIPTION OF THE INVENTION

Figure 1:
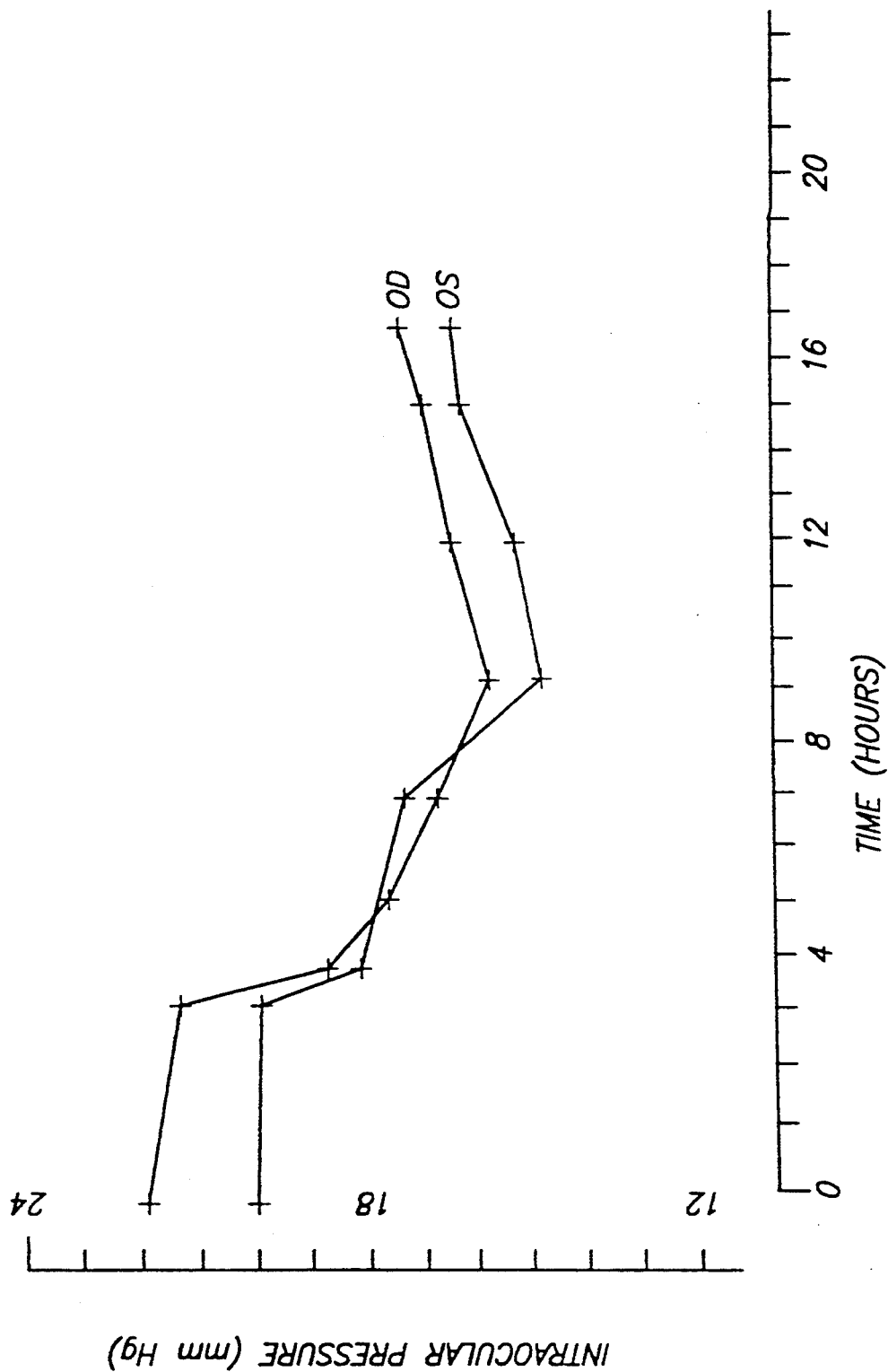
FIG. 1 shows in graphic form the effect on intraocular pressure of pilocarpine delivered according to the method of the invention as described in greater detail for Patient One in Example VIII.

According to one aspect of the present invention, a method of topical drug delivery is provided. According to this method, a desired drug is physically mixed with a pharmacologically acceptable carrier. The suitability of the carrier will be dictated both by its pharmacological acceptability for introduction into the eye and by the chemical characteristics of the desired drug. Although the carrier may be selected from a wide variety of compounds such as water-based solutions and gels, it is preferred to provide a carrier that is hydrophobic and that will not readily evaporate when brought into contact with the air. Petrolatum is particularly suitable as such a carrier. Like many of the lipids produced by the Meibomian glands, petrolatum is hydrophobic, will not evaporate, is an excellent solvent for lipids and is an excellent dispersing medium for both hydrophobic and hydrophilic compounds. Further, petrolatum is essentially inert and non-interactive with the tissues of the eye and can be obtained in a suitably pure state. Ophthalmological composition based on petrolatum and other water-free compounds is further preferred because it avoids the need for preservative agents.

The type of therapeutic agent or agents to be selected will depend primarily on the disease or disorder to be treated. These agents include a broad array of drugs currently delivered to the eye in topical fashion including, but not limited to, cyclosporine A, vitamin A alcohol, and testosterone, which are used to treat tear disorders; pilocarpine, beta blockers, and carbonic anhydrase inhibitors, which are used in the treatment of glaucoma; and antifungals and antivirals, which are used for the treatment of keratopathies. With regard to preparation of a drug-containing vehicle, it is within the knowledge of one skilled in the art to determine the correct amounts of drug to be added to the appropriate carrier in order to assure the efficacious delivery of the desired drug. It should also be noted that delivery of the desired therapeutic agent can be extended over time by selected a chemical form of the agent that is somewhat insoluble in water. The greater the insolubility, the longer the agent will take to dissolve and thus come into contact with eye tissue.

In the method of the invention, the drug/vehicle composition is manually placed on the extraocular skin adjacent to the lateral canthus using either one's finger or a suitable applicator, such as a cotton swab. Movements of the orbicularis oculi associated with the scissor-like closing of the lids transports a portion of the composition into the interpalpebral space. The drug is then released by dissolution into the tear film and from there passes into the eye through the corneal tissue. It will be appreciated that the amount of composition delivered to the extraocular skin region is not critical because only a small portion of the composition is consumed by each eye blink. The amount of composition to be delivered can depend therefore largely on the period of time desired between applications.

According to another aspect of the present invention, a topical drug comprising a minimally water-soluble, calcium-based composition that may be administered directly to the ocular surfaces or may be administered through the use of ocular inserts or by placing the composition on the skin of the lateral or inferior lid margins.

The composition itself is derived from a physical mixture of a poorly water-soluble calcium salt and a pharmacologically acceptable carrier. It is important that the calcium salt be very finely divided, preferably into microfine particles having a mean diameter of 60 microns or less. In one embodiment in which the composition carrier is hydrophobic, the mean particle diameter is 10 to 60 microns. In another embodiment in which the composition carrier is hydrophilic, the mean particle diameter is 10 microns or less. Division of the calcium salt into microfine particles may be accomplished by any standard means, such as pulverization in a mortar and pestle, or more simply by levigation with the polyol such as glycerol or propylene glycol.

It is also important that the calcium salt selected be largely insoluble in water. This will ensure a slow release over time of calcium ion into the tear film, thereby obviating the need for continuous or frequent application of the composition. Suitable calcium salts include calcium carbonate ($CaCO_3$), calcium tartrate ($CaC_4H_4O_6$), calcium magnesium carbonate ($CaCO_3 MgCO_3$), calcium metasilicate ($CaSiO_3$), calcium sulfate ($CaSO_4$), calcium malate ($Ca_4H_4O_5$), secondary calcium orthophosphate ($CaHPO_4$), and similar poorly water soluble calcium salts that are physiologically compatible and stable. Among these calcium carbonate, with a solubility of 0.0014 gm/100 ml in cold water, is preferred.

Turning now to the carrier, either hydrophobic or hydrophilic carriers are acceptable, although a hydrophobic carrier is preferred because it tends to be washed from the eye much less quickly than a typical hydrophilic carrier and can be applied to the external to the eye. As described more generally above, the preferred carrier for a drug therapeutic for dry eye is hydrophobic and sufficiently viscous to prevent dripping or running after application. Further, a water-free carrier may preclude the need for preservatives. Such a preferred carrier is petrolatum. The melting point of petrolatum may be increased by the admixture of a suitable substance such as white wax. Although less preferred, suitable, pharmacologically acceptable, hydrophilic carriers include physiological saline, with or without viscosity enhancing agents to delay wash-out, such a methyl cellulose, hydroxyethyl cellulose, hydroxypropylmethyl cellulose, carboxymethyl cellulose, polyethyleneoxide, and dextrans, along with any of the artificial tear formulations disclosed in the following United States Patents, the contents of which are herein incorporated by reference: U.S. Pat. Nos. 4,131,651, to Shah, et al.; 4,409,205 to Shively; 4,744,980 and 4,883,658, both to Holly; 5,075,104 to Gressel et al.

It will be apparent that the use of calcium ion to treat dry eye does not necessarily exclude the use of other known therapies. It should be possible to combine the delivery of calcium with that of other known therapies, such as the use of retinoids, estrogens, and the like. However, one must be careful to avoid compositions that include chelating or other binding agents having an affinity for ionic calcium.

The composition of the invention may be applied topically to the eye, either directly, indirectly or through the use of an ocular insert. Direct application to the eye surface is best accomplished by instilling a preparation of the composition that has a hydrophilic carrier, such as drops of a saline or artificial tear solution containing a calcium salt.

Although the above methods of application are possible, it is preferred to apply the composition extraocularly according to the general method of the invention by placing a small quantity of the composition on the skin adjacent to the lateral canthus. This enables the entrance of small volumes of the composition into contact with the fluid in the tear meniscus, and presumably thence into the preocular tear film. Although not wishing to be bound by any theory of operation, it is hypothesized that movement of the composition into the liquid between the interpalpebral space occurs through the interaction of several mechanisms. First, the petrolatum-based vehicle melts at body temperature without evaporating, resulting in a flow over the lid margin. Transport into the tear meniscus, and ultimately into the tear film, is probably accomplished by movement of the orbicularis orbis muscle of the lid, which causes medially-directed movement of the lower lid during the blink. Although the results of such passage have been shown by the relief of symptoms and signs, evidence of such action has also been gained by the application of the composition containing 6% sodium fluorescein in petrolatum. This soluble salt could be visualized four minutes after application and could be seen up to 40 minutes later. No fluorescence was observed during this interval following the placement of an identical ointment containing fluorescein acid.

The optimal active component is one that is miscible with the hydrophobic vehicle yet is water soluble. More effective action may be obtained from components that are potentially water soluble.

EXAMPLES

Example I: Preparation of Hydrophobic Composition

The calcium salt is finely divided by any standard means, such as pulverization in a mortar and pestle, or more simply by levigation with a polyol such as glycerol or propylene glycol. The finely divided powder or the polyol mixture is then admixed with a neutral ointment base such as petrolatum. In order to delay release of the calcium ion, substances with a higher melting point, such as white wax, may be admixed with the petrolatum to prolong passage of the preparation. A suitable hydrophobic preparation includes 2% to 25% weight by weight of the desired calcium salt.

Example II: Preparation of Hydrophilic Composition

The desired calcium salt is first pulverized as described in Example I. Either the finely divided calcium salt or the polyol mixture is then admixed with an appropriate aqueous solution such as normal saline or a mixture of sodium and potassium chlorides to mimic the ratio in normal tear fluid. The viscosity may be increased to suitable physiological levels by the addition of suitable viscosity increasing agents such as methyl cellulose, hydroxyethyl cellulose, hydroxypropylmethyl cellulose, carboxymethyl cellulose, ployethyleneoxide, and dextrans, along with any of the artificial tear formulations disclosed in the foregoing specification. A suitable hydrophobic preparation includes 0.05% to 5% weight by weight of the desired calcium salt.

Example III: Treatment Protocol

Hydrophobic Preparation

Frequency of use: once or twice daily, and following face washing.

Length of benefit: 3 hours or longer.

Degree of therapeutic benefit: significant alleviation of dry eye symptoms, including irritation, scratchiness and excessive tearing.

Hydrophilic Preparation

Frequency of use: 3–4 times daily.

Length of benefit: 2 hours or longer.

Degree of therapeutic benefit: significant alleviation of dry eye symptoms, including irritation, scratchiness and excessive tearing.

Example IV: Clinical Findings, Group I

A first group comprised three persons, two female and one male, ranging in ages from 60 to 70 years. No member of the group was a contact lens wearer. The females had keratoconjunctivitis sicca ("KCS") in varying severity, the male had chronic seborrheic tear film instability. Conventional treatment with tear substitutes provided transient relief at best.

To date, all have been successfully treated with daily application of the hydrophobic formulation of Example I for more than four months. There have been no detectable side effects.

Female I had long-standing KCS. She was treated by a single daily application of the hydrophobic formulation of Example I having a 10% weight by weight content of calcium carbonate. The formulation was applied to the skin immediately adjacent to each lateral canthus. Noticeable relief of symptoms occurred within 20 to 30 minutes later. Daily application was followed by complete disappearance of burning, itching, redness and epiphora. Reapplication was necessary on a daily basis and after face washing.

Female II had milder KCS than female I, exhibiting no epiphora. She was treated identically as female I. Signs and symptoms of KCS improved markedly following application of the formulation. Reapplication was necessary on a daily basis and after face washing.

Male I suffered from chronic seborrheic film instability. Male I was treated identically to Female I. After application, visual acuity improved from 20/40 to 20/20 or 20/15. Relief of symptoms was enhanced when the formulation was applied to margin of lower lid morning and at bedtime. Reapplication was necessary on a daily basis and after face washing.

Example V: Clinical Findings, Group II

A second patient population comprising 30 individuals ranging in ages from 45 to 88 years was studied. Two members of the group were diabetic, 1 was leukemic. All patients were selected on the basis of being chronic, poorly responsive to conventional treatments and exhibiting clinically obvious signs of tear problems such as bulbar injection and lid redness. Purely objective assessment of improvement was therefore possible from serial photographic records. Patients with tear meniscal widths less than 0.1 mm were excluded.

Each patient was treated with the hydrophobic composition of Example I containing 10% weight by volume of calcium carbonate. The composition was applied daily by the clinic ophthalmologist. Most patients were treated once daily at 8:00 am. The severest cases were treated three times a day. The longest course of treatment lasted 8 weeks. All but three patients showed objective and subjective improvement; of these, one did not return and two were discontinued after one week because of lack of objective improvement. Some patients required only once or twice weekly treatment. There were no allergic responses; no condition worsened.

Example VI: Effect of Other Divalent Cations

The effect of magnesium, the other main divalent cation in normal tears, on dry eye was studied. A hydrophobic composition according to Example I, containing 10% weight by weight of magnesium carbonate, was tested for its effect on symptoms and signs of dry eye. The composition was administered to each of the patients described in Example IV. No detectable improvement in either signs or symptoms was detected. The same results were obtained in a masked study on these same individuals.

Example VII: Pilocarpine Preparation

A hydrophobic composition containing pilocarpine was prepared according to the following protocol. The pilocarpine is obtained in acidic form as pilocarpine HCl and dissolved in glycerol. The glycerol-pilocarpine composition is then dispersed in petrolatum in a desired concentration by weight. In order to delay release of the pilocarpine, substances with a higher melting point, such as white wax, may be admixed with the petrolatum to prolong passage of the preparation. A suitable hydrophobic preparation includes 1–10% weight by weight of the pilocarpine.

Example VIII: Effect of Pilocarpine Delivery

In order to test the efficacy of the extraocular method of topical ophthalmic drug delivery of the present invention, a 4% pilocarpine ointment was prepared according to the protocol provided in Example VII. Approximately 50 mg of ointment was delivered extraocularly to a position adjacent to the lateral canthus of each patient. IOP and pupil diameter were measured immediately prior to application and at hourly intervals thereafter during the ensuing 18 hours.

Patient One was a male 49 years of age. Patient Two was a female 59 years of age.

The results for Patient One are shown graphically in FIG. 1. In this patient, pilocarpine was delivered to each eye according to the extraocular delivery method of the invention, and the effect on intraocular pressure followed for a period of 16 hours after administration. The effects of the pilocarpine on the reduction of intraocular pressure can be clearly observed for an extended period, demonstrating the effectiveness of the drug delivery method of the invention.

Figure 2:
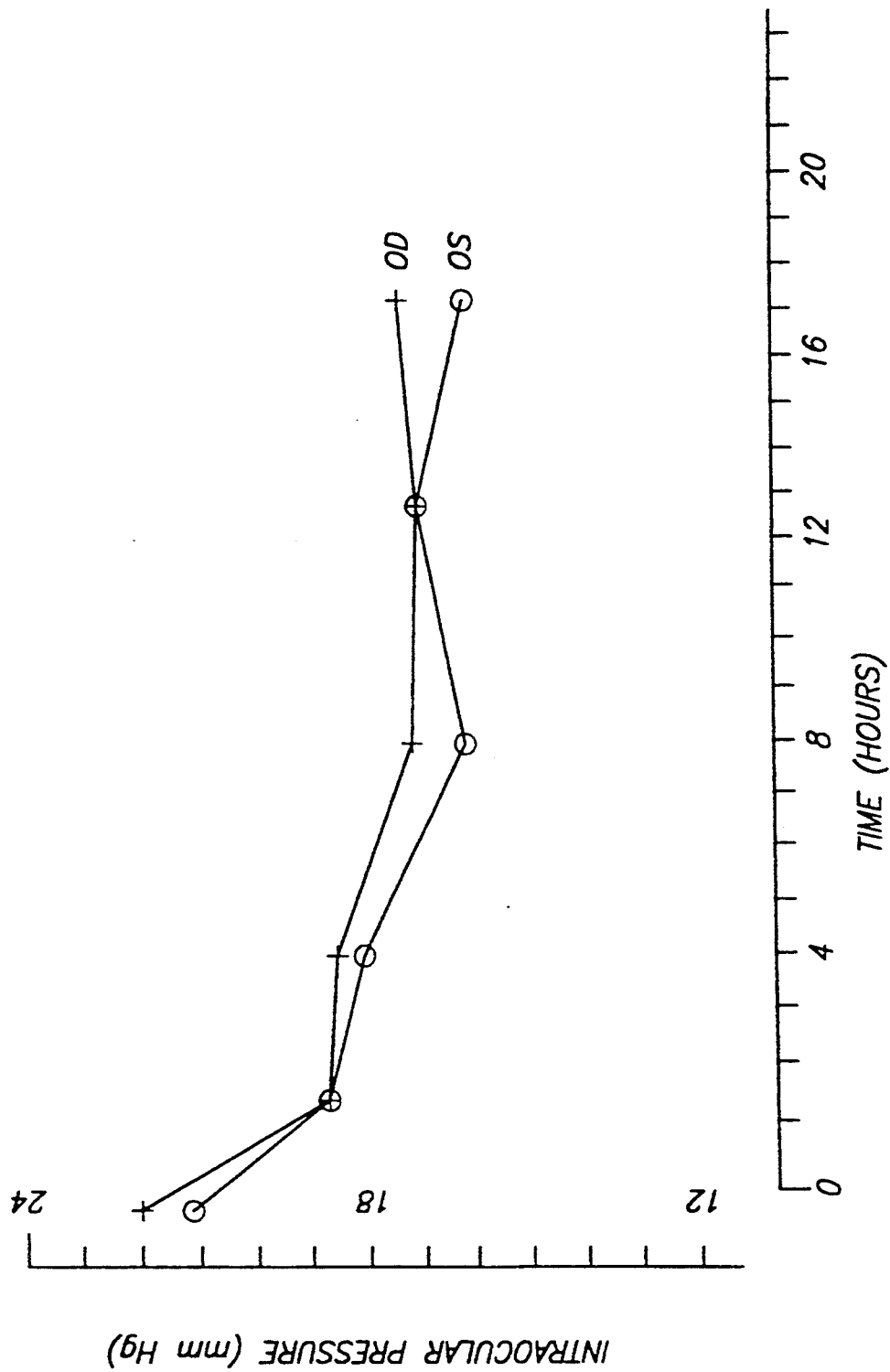
FIG. 2 shows in graphic form the effect on intraocular pressure of pilocarpine delivered according to the method of the invention as described in greater detail for Patient Two in Example VIII.

The results for Patient Two are shown graphically in FIG. 2. The results for Patient Two are shown graphically in FIG. 2. Pilocarpine was delivered to Patient Two according to the same protocol used with Patient One. Reduction in intraocular pressure following extraocular application of the pilocarpine ointment can be clearly observed.

From the foregoing, it can now be appreciated how the objects and features of the invention are met. The method of the invention provides a safe, efficient means of topical delivery of ophthamologically therapeutic agents over a prolonged period without the need for repetitive reapplication.

The method of the invention is clearly advantageous over the prior art in that extraocular delivery to the lateral canthus provides ease of administration, comfort, improved visual acuity during treatment, probable avoidance of the need for preservative agents in the therapeutic composition, minimal wash out of the therapeutic compound or existing tear film, minimal transconjunctival loss of drug, drug delivery to the optimal area for absorption, as well as minimal absorption across the conjunctiva.

According to another aspect of the invention, the method of the invention can be used to deliver a calcium-containing ointment to provide a ready source of calcium ion to the ocular surface. Because the ionic calcium is derived from a calcium salt that is minimally soluble in water, slow, long term release of ionic calcium into the tear film is effected.

The invention is clearly advantageous over known treatments in that long term relief of symptoms can be achieved with a minimum number of applications, generally once daily. Presently available dry eye treatments have durations of effectiveness that can be measured in mere minutes. According to Lemp (1972), the actual retention time of instilled artificial tears is in the order of minutes, a period inadequate to provide comfort for the severe dry eye patient. This situation has not significantly changed in the ensuing years.

The invention is generally advantageous in its ease of administration. The administration of conventional ophthalmic therapeutic preparations poses a problem especially for the older presbyopic patient. Proper placement of either drops or ointment without self-inflicted ocular injury can be difficult even to the normal sighted, requiring positional gymnastics and a steady hand. In contrast, the extraocular application at lid margins avoids the potential for injury that may result from delivery of therapeutic agents directly to the ocular surface.

Although the invention has been described with respect to a particular method of extraocular topical application of therapeutic agents and with regard to a specific calcium-bearing composition for treating dry eye syndrome, it will be appreciated that various modifications of the composition and method are possible without departing from the invention, which is defined by the claims set forth below.

I claim:

1. A method of topically delivering one or more therapeutic agents to the corneal surface of a human eye for the treatment or prevention of human ophthalmological diseases, said method comprising:
    a) providing an ophthalmological composition comprising a pharmacologically acceptable carrier having a viscosity sufficient to prevent said composition from dripping or running after said composition is applied and a therapeutically effective dose of one or more therapeutic agents combined with the carrier; and
    b) applying said ophthalmological composition to a position on skin adjacent to the lateral or inferior lid margins exterior to an ocular surface; wherein blinking action of the lid margins cuts off and carries into the eye small amounts of the composition thereby effecting treatment or prevention of human opthamological diseases.

2. The method of claim 1 wherein the pharmacologically acceptable carrier of said ophthalmological composition is hydrophobic.

3. The method of claim 2 wherein the pharmacologically acceptable carrier comprises petrolatum.

4. The method of claim 1 wherein the one or more therapeutic agents is selected from the group consisting of calcium salts, retinoids, testosterone, estrogen and their derivatives, anti-bacterial agents, anti-viral agents, anti-fungal agents, vitamin A alcohol, beta blockers and carbonic anhydrase inhibitors.

5. The method of claim 1 wherein a period of prolonged delivery of at least one hour is achieved following a single application of said ophthalmological composition.

* * * * *

UNITED STATES PATENT AND TRADEMARK OFFICE
CERTIFICATE OF CORRECTION

PATENT NO. : 5,366,739

DATED : November 22, 1994

INVENTOR(S) : MacKeen

It is certified that error appears in the above-indentified patent and that said Letters Patent is hereby corrected as shown below:

On the title page, item [22], the filing date should be --December 8, 1992--.

Signed and Sealed this

Fifth Day of March, 1996

Attest:

BRUCE LEHMAN

*Attesting Officer*     *Commissioner of Patents and Trademarks*